Figure 1:
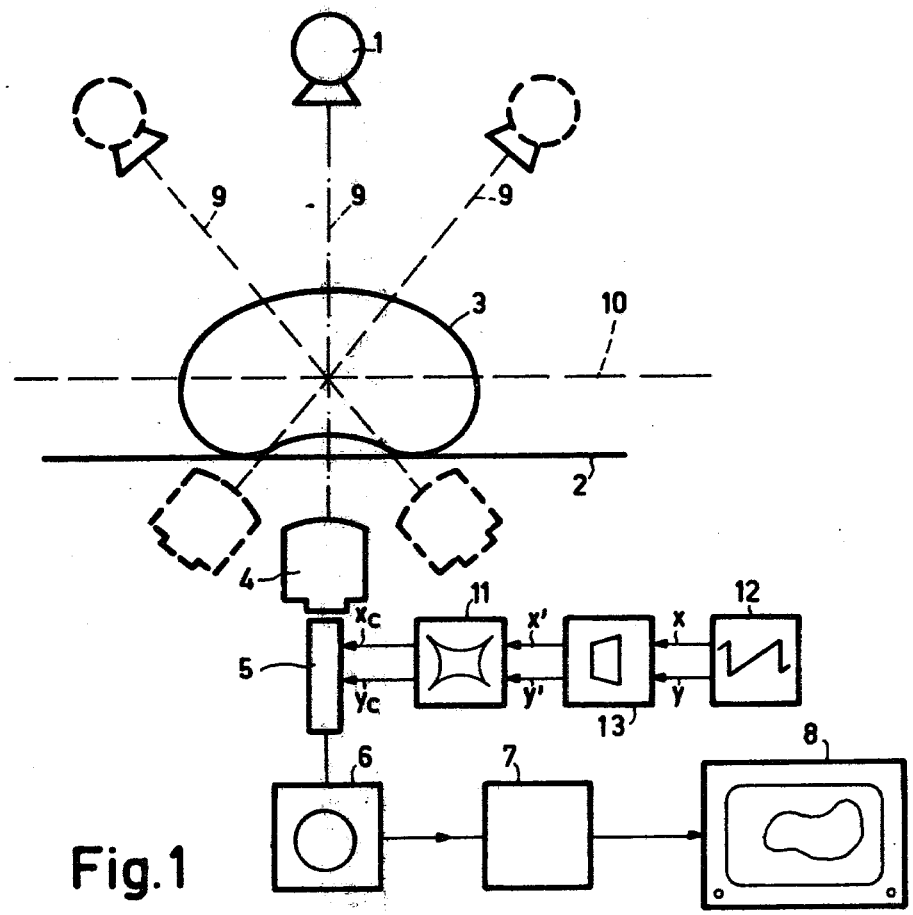

United States Patent [19]

Dittrich et al.

[11] 4,188,640
[45] Feb. 12, 1980

[54] APPARATUS FOR MAKING LAMINAR RADIOGRAMS

[75] Inventors: Jürgen Dittrich, Marschacht; Jürgen Heinzerling; Dietrich E. Meijer, both of Hamburg; Ralf Möllendorf, Ahrensburg; Friedrich Wolf, Marschacht, all of Fed. Rep. of Germany

[73] Assignee: U.S. Philips Corporation, New York, N.Y.

[21] Appl. No.: 862,689

[22] Filed: Dec. 21, 1977

[30] Foreign Application Priority Data

Dec. 23, 1976 [DE] Fed. Rep. of Germany ....... 2658331

[51] Int. Cl.² .............................................. H04N 5/32
[52] U.S. Cl. .............................. 358/111; 250/416 TV; 250/445 T
[58] Field of Search ................. 358/110, 111; 250/312, 250/313, 320, 321, 322, 323, 416 TV, 445 T

[56] References Cited

U.S. PATENT DOCUMENTS

| | | | |
|---|---|---|---|
| 3,499,146 | 3/1970 | Richards | 250/323 |
| 4,146,794 | 3/1979 | Duinker | 358/111 |

Primary Examiner—Robert L. Griffin
Assistant Examiner—Edward L. Coles

Attorney, Agent, or Firm—Thomas A. Briody; Edward J. Connors, Jr.; Jack E. Haken

[57] ABSTRACT

In tomosynthesis, as is known, a series of individual images taken in different orientations, are superimposed. By shifting the individual images relative to each other the position of the layer which is sharply reproduced can be changed. However, there may still be unsharpness in said layer, in the case of image distortion during recording of the individual images, for example owing to the curvature of the input screen. This image distortion can hardly be compensated for, because it greatly depends on the projection angle. The invention provides a simple method of compensating for such image distortion. The image intensifier is then arranged and steered so that its optical axis is always parallel to the central ray. The distortion caused by the image intensifier curvature is then independent of the projection angle and can be eliminated in a comparatively simple manner. Steering the image intensifier in this way gives rise to additional distortion, because the planes, of which subsequently laminar radiograms are made by superposition, and the optical axis of the image intensifier are no longer perpendicular to each other. However, this is a simple geometric distortion which can be eliminated in a simple manner.

6 Claims, 2 Drawing Figures

APPARATUS FOR MAKING LAMINAR RADIOGRAMS

The invention relates to apparatus for making laminar radiograms with an image recording device, which comprises an image intesifier and a television camera for recording individual images in different positions of the X-ray radiator and of the image recording device, and with a super-position device for the formation of a laminar radiogram by the superposition of the individual images which have been shifted relative to each other by predetermined amounts.

Such apparatus is known (compare for example DT-OS No. 17 64 414 and U.S. Pat. Ser. No. 3,499,146). In this apparatus a series of individual images from different directions of projection are superimposed. The superposition image only gives a sharp reproduction of a thin layer of the object. Laminar radiograms of other planes of the object can be produced, in that the individual images are shifted relative to each other to an accurately defined extent prior to superposition. However, perfectly sharp laminar radiographs are then obtained only if prior to superposition the individual images can be recorded and further processed without any geometric image distortion.

The use of an image intensifier, which converts the X-ray shadow image into a visible image with increased brightness, and a camera tube which converts the image on the output screen of the image intensifier into a video signal, gives rise to considerable image distortions. These distortions arise as a result of distortions which are caused by the electron-optical systems in the image intensifier and in the camera tube and are independent of the geometric conditions during recording, and as a result of distortions which depend on the projection of the object onto the generally spherically curved input screen of the X-ray image intensifier. In apparatus of the type mentioned in the preamble this distortion component greatly depends on the projection angle.

An electronic method for the correction of such image distortions is known from DT-OS No. 24 37 529. According to this method correction voltages are superimposed on the deflection voltages for the camera tube or a storage tube included in the superposition device, which correction voltages are produced by a computer-controlled correction-network. This method is complicated and very difficult to realize, because the parameters of the image distortion to be compensated for change from image to image depending on the projection angle.

It is an object of the present invention to construct an apparatus of the type mentioned in the preamble in such a way that image distortions of the individual images are reduced in a simple manner.

According to the invention this object is achieved in that the image recording device is arranged and steered so that its optical axis is always parallel to the central ray, that there is provided a correction device which reduces distortions arising as a result of the construction of the image recording device, and that during read-in of an individual image the deflection voltages or currents for the television camera or for an image storage tube which serves for superposition can be modified in such a way, depending on the laminar angle and the orbit angle, that geometric distortions arising as a result of the slope of the input screen of the image intensifier relative to the laminar plane are compensated for.

In known apparatus of the type mentioned in the preamble the image recording device is steered so that its optical axis always intersects the laminar plane perpendicularly, so that the optical axis and the central ray, which connects the focus of the X-ray tube to the centre of the image-intensifier input screen, make an angle which differs from zero with each other. On this condition only is it achieved that all parts of a lamina of the object are sharply reproduced in the superposition image, whilst moreover assuming that the image recording device represents a flat projection plane.

However, in accordance with the invention the image recording device is steered in such a way that its optical axis remains parallel to the central ray (which can for example be achieved in a simple manner in that the image recording device is secured to a guide rod in a suitable manner, which rod provides the mechanical coupling between the X-ray tube and the image recording device), so that the laminar plane and the plane of the input screen of the image intensifier together make an angle with each other which is equal to the laminar angle (which is the angle between the central ray and the normal to the laminar plane). The invention is based on the recognition that with such a steering distortions as a result of the construction of the image recording device (distortions as a result of the electron-optical system as a result of the coupling objective between the output screen of the image intensifier and the television camera, owing to the curvature of the image intensifier input screen etc.) in contradistinction to the known apparatus - become independent of the geometrical relations during recording and can thus be compensated for in a much simpler manner.

Correction devices by means of which distortions as a result of the construction of the image recording device can be compensated for, are already commercially available. If laminar images are to be derived from the corrected images by superposition, an additional image correction operation is to be performed, by means of which the projection plane which is normal to the central ray is rotated in the projection plane which is perpendicular to the normal to the laminar plane. The magnitude of this image correction depends on the laminar angle $\alpha$. However, this is a comparatively uncomplicated trapezium correction (i.e. a rectangle in the laminar plane, whose sides respectively extend parallel and perpendicularly to the projection of the central ray on the laminar plane, is imaged as a trapezium in a plane which is perpendicular to the central ray). Moreover, the amount of correction is small. For example, for a projection angle range of $\alpha = \pm 15°$ and an image diameter of 1/10 of the X-ray tube focus/image distance the image is to be extended 1/cos 15°. In addition, a trapezium correction of only approx. $\pm 1.3\%$ is necessary. This correction can be superimposed on the beam deflection of the television camera tube. However, it may also be superimposed on the beam deflection of an image storage tube used for image summation (superposition) during write-in of the individual projection images.

The geometric distortions are eliminated in that during scanning of the individual image on the target of the television camera or during read-in of the individual image in for example an image storage tube which serves for the superposition of the individual images the deflection voltages or deflection currents are dependent on the laminar angle and the orbit angle (which is the angle which the projection of the central ray on the laminar plane makes with a straight line which is preferably parallel to the line-scanning direction). The field to be scanned of the television camera is then deformed in the same way as a rectangle in the laminar plane is deformed owing to the geometric distortion. However, the deflection field of for example an image storage tube, in which the video signals corresponding to the individual images are stored for the purpose of superposition and formation of a laminar radiogram, is to be deformed inversely, i.e. (areas) which are expanded by the projection should be contracted and vice versa.

In accordance with a further embodiment of the invention the deflection voltages or deflection currents are applied to the deflection units of the television camera via a computing device, which modifies the x and y deflection voltages or deflection currents of a deflection generator by $$u = x \cdot \cos \varphi + y \cdot \sin \varphi$$

$$k_1 = \cos \alpha - 1$$

$$k_2 = -(1/a) \sin \alpha,$$

through an additive correction in accordance with the relationship $$x' = x + k_1 \cdot u \cdot \cos \varphi + k_2 \cdot u \cdot x + k_1 \cdot k_2 \cdot u^2 \cos \varphi \quad (1)$$

and $$y' = y + k_1 \cdot u \cdot \sin \varphi + k_2 \cdot u \cdot y + k_1 \cdot k_2 \cdot u^2 \sin \varphi \quad (2)$$

where $x'$, $y'$ are the deflection voltages or currents applied to the deflection units, $\varphi$ is the orbit angle, $\alpha$ the laminar angle, and $a$ a constant which corresponds to the distance of the focus of the X-ray tube to the image-intensifier input screen. Solving the above-mentioned equations with respect to x and y yields the relationship in accordance with which the respective deflection voltages or currents ($x'$, $y'$) of a deflection generator are to be modified during read-in of the individual images into for example an image storage tube, so that the corresponding deflection units receive such deflection voltages and currents (x, y) that the said geometric distortions are eliminated.

The invention will now be described in more detail with reference to the drawing which shows an embodiment. In the drawing FIG. 1 schematically represents an embodiment of the invention, FIG. 2 is an example of a circuit included between the deflection generator and the deflection unit of the television camera, which modifies the deflection voltages or deflection currents supplied by the deflection generator in accordance with the equations (1) and (2).

Figure 2:
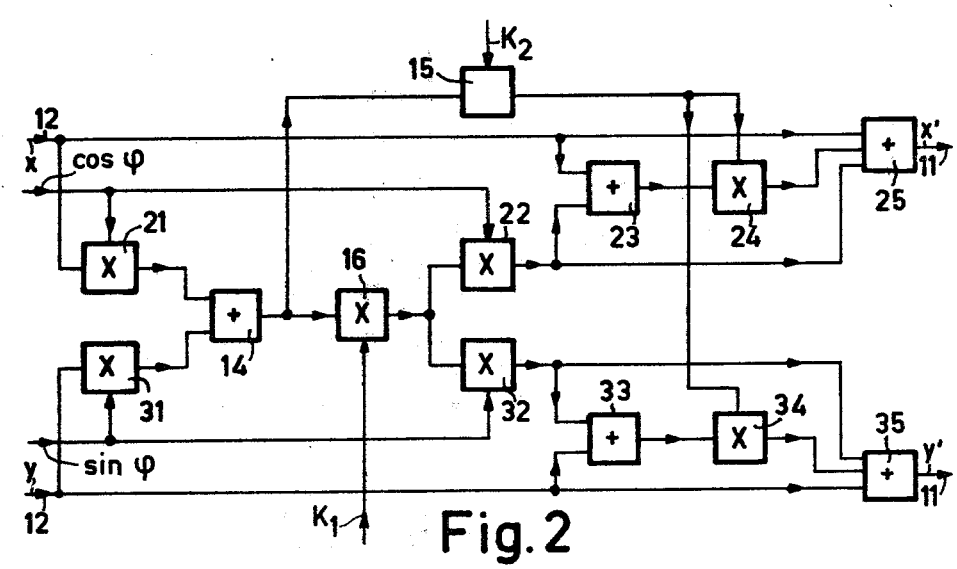

In FIG. 1 an X-ray source is designated 1, whose radiation passes through the body of a patient 3 which is positioned on a table top 2. The ray transmission behind the patient is intercepted by an image intensifier 4 and converted into a visible image, which is recorded by a television camera 5. The signals then produced, which each correspond to an individual image, are transferred into a buffer memory 6, for example a disc memory, from which they can be extracted and stored in an image storage tube 7 for the formation of a superposition image. The relative shift of the individual images, which depends on the position of the laminar plane to be reproduced by superposition, is then computed by a control computer, not shown, which also controls the deflection units of the image storage tube 7 accordingly. The laminar radiogram obtained by superposition can be read from the target of the image storage tube 7 and displayed by an image display unit 8. So far the construction of the apparatus shown in FIG. 1 is known.

The individual images are taken in different positions of the system radiator image-recording device (image intensifier 4 and television camera 5). FIG. 1 shows three of these positions, two positions being represented by dashed lines only. The points of intersection of central rays 9 determines the position of the plane 10 that can be reproduced sharply by superposition of the individual images without relative displacement.

In FIG. 1 it can be seen that the image recording device is steered so that its optical axis (which is the line which is perpendicular to the centre of the image-intensifier input screen) always extends parallel to the central ray 9, whilst in known apparatus the image recording device is arranged so in the various positions, that its optical axis is perpendicular to the laminar plane 10. Steering the image-recording device in such a way that its optical axis extends parallel to the central ray is simple, because most tomography equipment comprises a coupling rod which links the X-ray radiator and the image recording device to each other and causes them to be moved in opposite directions. This coupling rod extends parallel to the central ray, and therefore it need only be linked to the image-recording device in such a way that it extends parallel to the optical axis of the image recording device.

In this arrangement of the image recording device the image distortion owing ot the curvature of the image-intensifier input screen, owing to the electronics, owing to the coupling objective, not shown, between the output screen of the image intensifier and the television camera etc. is the same for all positions of the system radiator/image recording device and is independent of the angle at which the central ray 9 intersects the laminar plane 10. Therefore, it can be eliminated by commercially available correction devices (for example, "INTRONIX pin-cushion distortion module" from Mssrs. Infraton, Munich).

These correction devices, which are for example employed for correcting the image geometry in high-resolution cathode-ray tubes, derive distorted deflection voltages $x_x$ and $y_c$ from the deflection voltages or deflection currents $x'$, $y'$, the distortion of the deflection voltages being adjustable in such a way that the distortion caused by the curvature of the image-intensifier input screen etc. can be eliminated. The apparatus in accordance with FIG. 1 comprises such a correction device 11, whose inputs are connected to the outputs of a deflection generator 12 via a circuit 13 whose function is to be explained hereinafter, and whose outputs are connected to the deflection units of the television camera 5.

As previously stated, additional geometric distortion is produced as a result of the slope of the image intensifier input screen relative to the laminar plane. As an example, in the positon of the X-ray radiator and the image recording device in which the X-ray radiator is located at the left and the image intensifier at the right, the areas of the laminar plane to the right of the intersection with the central ray are imaged smaller than those situated to the left of the intersection, because the areas situated to the right of the central ray are situated nearer the image intensifier input screen. It can be demonstrated that a point situated in the laminar plane 10, which point corresponds to the coordinates x, y in the case of the usual parallel projection on the image-intensifier input screen, is imaged in a plane (corresponding to the image-intensifier input screen) which is perpendicular to the central ray 9, as a point with the coordinates x', y' (the zero point of the coordinate system x, y and x', y' being situated on the central ray 9), for which as an approximation the following relationship is valid:

$$x' = x + k_1 \cdot u \cdot \cos\varphi + k_2 \cdot u \cdot x + k_1 \cdot k_2 \cdot u^2 \cos\varphi$$

and $$y' = y + k_1 \cdot u \cdot \sin\varphi + k_2 \cdot u \cdot y + k_1 \cdot k_2 \cdot u^2 \sin\varphi$$

where $$u = x \cdot \cos\varphi + y \cdot \sin\varphi$$

$$k_1 = \cos\alpha - 1 \text{ and}$$

$$k_2 = -1/a \sin\varphi$$

Therein $\varphi$ is the orbit angle, i.e. the angle enclosed by the projection of the central ray 9 on the laminar plane and the x-axis, $\alpha$ the laminar angle, and a the distance of the focus of the X-ray radiator from the image intensifier input-plane.

These geometric distortions can be eliminated, when the deflection voltages or deflection currents in the x and y direction, which are also designated x and y in this case, are modified into x' and y' in accordance with the equations (1) and (2). The deflection voltages or currents of the storage tube 7 and the display unit then remains undistorted. The quantities x' and y' not only depends on x and y respectively, but also an y and x. This means that when x is the horizontal deflection voltage or the horizontal deflection current and y the vertical deflection voltage or the vertical deflection current, the modified quantity x', in addition to the horizontal frequency components, also comprises components of vertical frequency and that the modified quantity y', in addition to components of vertical frequency, also contains horizontal-frequency components, whose magnitude depends on the orbit angle $\varphi$ and the laminar angle $\alpha$.

The circuit arrangement 13 modifies the sawtooth-shaped horizontal and vertical deflection voltages or currents in accordance with the equation (1) into voltages or currents x' and y', so that geometric distortion as a result of the slope of the image-intensifier input screen relative to the laminar plane is eliminated. The modified voltages or currents x' and y' are applied to the previously described correction device 11, which derives therefrom the deflection voltages or deflection currents $x_c$ and $y_c$ for the deflection units of the television camera 5 and thus also eliminates distortion as a result of the curvature of the image-intensifier input screen etc.

FIG. 2 shows an example of the circuit arrangement 13 for eliminating geometric distortion. The deflection voltages or the deflection currents x and y from the deflection generator 12 are applied to an adder stage 25 and 35 respectively, and to a multiplier circuit 21 and 31 respectively, in which they are multiplied by $\cos\varphi$ and $\sin\varphi$ respectively. The output signals of the two multiplier circuits 21 and 31 are applied to the inputs of an adder circuit 14, so that the output signal of this circuit, which is applied to the two multiplier circuits 15 and 16, corresponds to the quantity u in equations (1) and (2). In the multiplier circuit 16 the output signal of the adder circuit 14 is multiplied by the value $k_1$. The output of the multiplier circuit 16 is connected to an input of the multiplier circuit 22 and 32 respectively, in which circuits the output signal of the multiplier circuit 16 is multiplied by $\cos\varphi$ and $\sin\varphi$ respectively. Hence, the output signal of the circuits 22 and 32 corresponds to the second term in equations (1) and (2) respectively. It is applied to a further input of the adder circuits 25 and 35 respectively and moreover to an adder circuit 23 and 33 respectively, which adds the output signal of 22 or 32 to the input quantity x or y respectively. The output signal of the circuits 23 and 32 is multiplied by the output signal of the multiplier circuit 15 in a multiplier circuit 24, which circuit 15 in its turn multiplies the output signal of the circuit 14 by the factor $k_2$. The output signal of the multiplier circuit 24 or 32 then corresponds to the sum of the third and fourth terms in equations (1) and (2) respectively. It is applied to a further input of the adder circuit 25 and 35 respectively, so that at the ouput thereof the respective quantity x' or y' is available.

Special advantages are obtained when the multiplier stages 15, 16, 21, 22, 31, and 32 are replaced by so-called multiplying digital-to-analog converters (for example "Multiplying D/A Converters" from Analog Devices, Norwood, Mass., USA), which in respect of their accuracy and bandwidth are highly superior to analog multipliers. The correction parameters $k_1$, $k_2$, $\cos\varphi$, and $\sin\varphi$ should then be made available in digital form. The parameters $k_1$ and $k_2$ can now readily be calculated by the control computer, which is needed anyway in such apparatus. They are constant in the case of a circular blurring pattern. The values $\cos\varphi$ and $\sin\varphi$ vary from individual image to individual image- at any rate when the system radiator/image recording device is not positioned along a straight line during recording of the various individual images. Therefore, they have to be recalculated for each individual image. When the angle $\varphi$ is measured digitally during recording, the angular functions can be determined by means of tables stored in fixed-programme semiconductor memories. The periodicity and the symmetry of the angular functions enables both angular functions in all four quadrants to be calculated by means are a table for one quadrant only.

What is claimed is:

1. An apparatus for producing laminar radiograms, including an X-ray radiator and an image recording device mounted to image a subject at different positions with the optical axis of the image recording device maintained parallel to the central ray of the X-ray radiator, the image recording device including an image intensifier and a television camera for recording images of said image intensifier, and further including a superposition device coupled to the television camera for forming laminar radiograms corresponding to images in a laminar plane by superposing individual images which have been shifted by determined amounts with respect to one another; the improvement comprising a correction means coupled to reduce distortion resulting from the structure of aid image recording device, and further comprising deflection signal modifying means for modifying deflection signals in said apparatus as a function of the laminar angle $\alpha$ and the orbit angle $\varphi$ to correct for geometric distortion resulting from the slope between the input screen of the image intensifier and the laminar plane, the orbit angle $\varphi$ being the angle between the projection of the central ray on the laminar plane and the X-axis, and the laminar angle $\alpha$ being the angle between the central ray and the normal to the laminar plane.

2. The apparatus of clam 1 wherein said superposition device includes an image storage tube for the formation of superposition images, said correction means and signal modifying means being coupled to said apparatus whereby images stored in said storage tube are corrected with respect to said geometric distortion and distortion resulting from the structure of said image recording device.

3. The apparatus of claim 1 wherein said correction means comprises pin-cushion distortion correction means.

4. The apparatus of claim 1 comprising a source of deflection signals for said apparatus, wherein said signal modifying means comprises a computing device connected to modify the deflection voltages or currents of said deflection signal source in accordance with the relationships $$x' = x + k_1 \cdot u \cdot \cos \varphi + k_2 \cdot u \cdot x + k_1 \cdot k_2 \cdot u^2 \cdot \cos \varphi$$

and $$y' = y + k_1 \cdot u \cdot \sin \varphi + k_2 \cdot u \cdot y + k_1 \cdot k_2 \cdot u^2 \sin \varphi$$

wherein $$u = x \cdot \cos \varphi + y \cdot \sin \varphi$$

$$k_1 = \cos \alpha - 1$$

$$k_2 = -(1/a) \sin \alpha$$

x and y being the deflection voltages or currents of said deflection signals, x' and y' being the modified deflection voltages or currents, and a being a constant corresponding to the distance of the focus of the X-ray tube to the image intensifier input screen.

5. The apparatus of claim 1 wherein said superposition device includes a storage tube, said correction means signal modifying means being coupled to said apparatus to remove distortions before application of signals to said storage tube.

6. The apparatus of claim 1 wherein said correction means and signal modifying means are serially connected with respect to one another to modify deflection voltages or currents of said television camera.

* * * * *